(12) United States Patent
Pollack et al.

(10) Patent No.: US 8,614,739 B2
(45) Date of Patent: Dec. 24, 2013

(54) APPARATUS AND METHOD FOR ANALYZING FLUIDS IN VESSELS AND PIPELINES

(75) Inventors: Michael J. Pollack, Lansdale, PA (US); Branson J. Darnell, Perkiomenville, PA (US); Richard A. DiDomizio, Hatfield, PA (US); William Rollin, III, Hatboro, PA (US)

(73) Assignee: Pollack Laboratories, Inc., Colmar, PA (US)

(*) Notice: Subject to any disclaimer, the term of this patent is extended or adjusted under 35 U.S.C. 154(b) by 940 days.

(21) Appl. No.: 12/650,963

(22) Filed: Dec. 31, 2009

(65) Prior Publication Data

US 2011/0157351 A1    Jun. 30, 2011

(51) Int. Cl.
H04N 7/18 (2006.01)

(52) U.S. Cl.
USPC .......................................................... 348/84

(58) Field of Classification Search
USPC .................. 382/120, 122; 348/61, 82, 84, 85; 137/559
See application file for complete search history.

(56) References Cited

U.S. PATENT DOCUMENTS

| | | |
|---|---|---|
| 3,809,607 A | 5/1974 | Murrey et al. |
| 4,393,466 A | 7/1983 | Deindoerfer et al. |
| 4,659,218 A | 4/1987 | de Lasa et al. |
| 4,814,868 A | 3/1989 | James |
| 4,893,935 A | 1/1990 | Mandel et al. |
| 4,965,601 A | 10/1990 | Canty |
| 4,977,418 A | 12/1990 | Canty |
| 5,152,175 A | 10/1992 | Reynolds |
| 5,182,791 A | 1/1993 | Pollack |
| 5,230,556 A | 7/1993 | Canty et al. |
| 5,425,279 A | 6/1995 | Clark et al. |
| 5,561,520 A | 10/1996 | Williams |
| 5,956,077 A | 9/1999 | Qureshi et al. |
| 6,049,381 A | 4/2000 | Reintjes et al. |
| 6,111,599 A | 8/2000 | Nance et al. |
| 6,122,042 A | 9/2000 | Wunderman et al. |
| 6,252,980 B1 | 6/2001 | Schwartz et al. |
| 6,450,655 B1 | 9/2002 | Walck et al. |
| 6,501,072 B2 * | 12/2002 | Mullins et al. ................ 250/256 |
| 6,603,117 B2 | 8/2003 | Corrado et al. |
| 6,629,449 B1 | 10/2003 | Kline-Schoder et al. |
| 6,660,995 B1 | 12/2003 | Canpolat et al. |
| 6,673,532 B2 | 1/2004 | Rao |
| 6,723,981 B2 | 4/2004 | Corrado et al. |
| 6,782,184 B2 | 8/2004 | Canty et al. |
| 6,806,900 B2 | 10/2004 | Eversole et al. |

(Continued)

Primary Examiner — Richard Torrente
(74) Attorney, Agent, or Firm — Howson & Howson LLP

(57) ABSTRACT

Apparatus for analyzing fluid or surfaces within a pipeline or vessel includes a probe positioned to capture or record images through a viewing port of the pipeline/vessel and an illumination assembly arranged to illuminate the fluid/surfaces within the pipeline/vessel adjacent the port with visible, infrared or ultraviolet light of a predetermined wavelength or within a predetermined range of wavelengths. Depending upon the type of fluid, light or radiation of a particular wavelength may be required to capture an image of high contrast and clarity. Accordingly, an electronic controller communicates with the probe and the illumination assembly for automatically controlling operation thereof so that images are captured and recorded of the fluid illuminated with light of different predetermined wavelength or predetermined range of wavelengths. An analyzing unit analyzes the images and identifies an image of greatest level of contrast or clarity and the wavelength or predetermined range of wavelengths of the light used to illuminate the fluid for the image of greatest level of contrast or clarity. A method is also disclosed.

9 Claims, 5 Drawing Sheets

(56) References Cited

U.S. PATENT DOCUMENTS

| | | |
|---|---|---|
| 6,888,631 B2 | 5/2005 | Eriksson |
| 6,960,756 B1 | 11/2005 | Penumadu et al. |
| 7,041,493 B2 | 5/2006 | Rao |
| 7,079,242 B2 * | 7/2006 | Bordelon .................... 356/336 |
| 2002/0101508 A1 | 8/2002 | Pollack |
| 2004/0095577 A1 | 5/2004 | Eckardt et al. |
| 2005/0046841 A1 | 3/2005 | Rabinski et al. |
| 2005/0134845 A1 | 6/2005 | Bordelon |
| 2006/0017930 A1 | 1/2006 | Canty et al. |
| 2006/0152730 A1 | 7/2006 | Schneider |
| 2006/0256340 A1 | 11/2006 | Hansen et al. |
| 2007/0035736 A1 * | 2/2007 | Vannuffelen et al. ......... 356/432 |
| 2008/0143828 A1 | 6/2008 | Mandrachia et al. |
| 2008/0158374 A1 * | 7/2008 | Sapia ...................... 348/222.1 |
| 2008/0166037 A1 | 7/2008 | Mandrachia et al. |
| 2008/0252881 A1 * | 10/2008 | Yakimoski et al. ........... 356/246 |

* cited by examiner

APPARATUS AND METHOD FOR ANALYZING FLUIDS IN VESSELS AND PIPELINES

BACKGROUND OF THE INVENTION

The present invention relates to analyzing the characteristics of a fluid within in a vessel or flowing within a sealed pipe, conduit, or the like and more particularly, the present invention relates to real-time determination of the type and/or grade of fluid, the presence and characteristics of foreign matter such as droplets, bubbles, particles and the like within the fluid, and/or the presence of contaminants, corrosion or the like within or on the interior walls of the vessel, pipeline or other sealed hollow apparatus.

By way of example, knowledge of the types and characteristics of fluid flowing within a sealed pipeline and/or like conduit provides numerous benefits. For instance, it is often necessary and/or beneficial in various industries to confirm and/or make a determination as to the type, grade and/or characteristics of a fluid actually present and flowing within a sealed section of a pipe or like conduit without disrupting the flow or on-going operation. It is also beneficial to have an understanding of the type, amount and characteristics of any foreign materials carried by the fluid flow. Such foreign materials may include solid particles, liquid droplets, gas bubbles and the like.

By way of specific example, it is often necessary or desirable in the oil industry to determine the type or grade of crude oil or like liquid flowing within a given section of sealed pipeline at any particular time. With respect to crude oil, it may be a relatively dark, murky, opaque type of liquid that is difficult to visualize with any degree of meaningful optical resolution. It is also typically desirable to determine the type, size and/or amount of foreign matter carried by the fluid flow, such as water droplets, gas bubbles or other particulates. For instance, the amount of iron oxide particulate matter flowing within a pumped fluid may provide an indicator that a nearby pump requires maintenance and/or that the period between maintenance services for the pump should be reduced and/or can be extended.

In addition to fluids flowing in pipelines, it may also be advantageous to ascertain the characteristics of fluids within sealed or unsealed vessels, such as reactors, chemical reactors, fermentors, bio-fermentors, towers, fractioning towers, tanks, vats and the like. The fluids may be liquids, powders, particulate material such as resin particulates, sand, gas, or any other flowable fluid. Also, between cleanings of such vessels, it may be advantageous to view the internal walls or other surface areas within the vessels to determine the presence or lack thereof of contaminants, corrosion, or the like. In various industries, the important contaminants to identify, such as the residue of organic materials or the like, are typically difficult to visualize under ambient light While known monitoring and inspection systems may function in an acceptable manner, there continues to be a need for improved systems and methods enabling ready, easy, accurate and efficient monitoring of fluid flowing within pipelines or contained within vessels. The monitoring of such fluids should provide real time determinations as to type of fluid and the characteristics of any foreign matter carried thereby. Analysis with respect to contaminants and the like on interior surfaces of the vessels or pipes should also be provided. This is particularly applicable to fluids flowing in sealed pipelines and/or vessels in which physical access to the fluid or interior surfaces of the pipelines/vessels is difficult or undesirable and/or to fluids that may be dark and murky and difficult to visualize with any degree of clarity in ambient light.

SUMMARY OF THE INVENTION

According to one aspect of the present invention, apparatus for analyzing fluid flowing within a sealed pipeline or contained within a vessel or for analyzing interior surfaces of the pipeline or vessel is provided. A section of the pipeline/vessel has at least one viewing port, and a probe is positioned to capture or record images through the viewing port of fluid flowing or present within the section of pipeline/vessel and/or of the interior surfaces of the pipeline/vessel. The apparatus includes an illumination assembly arranged adjacent the pipeline/vessel to illuminate the fluid or surfaces within the section of pipeline/vessel adjacent the port with visible, infrared or ultraviolet light of a predetermined wavelength or within a predetermined range of wavelengths. Depending upon the type of fluid, light or radiation of a particular wavelength may be required to capture a meaningful image of high contrast and clarity. This is also true when images of various types of contaminants, residues or the like on interior surfaces of the pipeline/vessel are desired. Accordingly, an electronic controller is in communication with the probe and the illumination assembly for automatically controlling operation thereof so that images are captured and recorded of the fluid or surfaces illuminated with light of different predetermined wavelength or predetermined range of wavelengths. The apparatus also includes an analyzing unit for analyzing the images illuminated with light of different predetermined wavelength or predetermined range of wavelengths and for identifying an image of greatest level of contrast or clarity and the wavelength or predetermined range of wavelengths of the light used to illuminate the fluid for the image of greatest level of contrast or clarity.

The illumination assembly includes a light source directing visible, infrared, or ultraviolet light into a monochromator. The controller is in communication with the monochromator and controls the predetermined wavelength or predetermined range of wavelengths of light transferred into the pipeline/vessel by the monochromator and records the value or values of the predetermined wavelength or predetermined range of wavelengths relative to each image captured by the probe.

The analyzing unit can include image recognition software for determining the level of contrast or clarity of each of the captured images so that a light absorption point of the fluid is determinable based on the wavelength or range of wavelengths of light used to illuminate the image of greatest level of contrast or clarity. In this manner, a type or grade of the fluid is determined or confirmed based on the light absorption point determined for the fluid. Also, the presences or lack thereof of particular contaminants, residues or the like on interior surfaces of the pipeline/vessel can be determined.

The image recognition software can also be used to determine the presence, type, and characteristics of gas bubbles, solid particulates, and liquid droplets of foreign matter in the fluid or on the interior surfaces. The type of the foreign matter can be determined by measuring the refractive index of each spot of foreign matter appearing in the image of greatest level of contrast or clarity and by comparing the measured refractive index with known refractive indexes of various foreign matters.

The controller and analyzing unit can be provided as a computer or like electronic processor. The computer is linked to the camera of the probe, the monochromator, and the light source for controlling the operation thereof and for receiving and recording images taken by the camera in real time. In addition, the image recognition software of said computer can analyze the images in real time and make the above referenced measurements and determinations in real-time without disturbing the flow of the fluid in the pipeline or an on-going process occurring within a vessel.

According to another aspect of the present invention, a method of analyzing fluid/interior surfaces within a pipeline/vessel is provided. An image of fluid/interior surfaces within the pipeline/vessel is recorded with an optical probe via a viewing port of the pipeline. During the recording step, the fluid/surfaces in the pipeline/vessel is illuminated adjacent the viewing port with light of a predetermined wavelength or predetermined range of wavelengths and the value or values of the predetermined wavelength or predetermined range of wavelengths is recorded for the image. The illuminating and image recording steps are repeated a plurality of times in which each illuminating step is accomplished with light of different predetermined wavelength or predetermined range of wavelengths. A determination is made as to which recorded image is of greatest contrast or clarity to thereby determine a light absorption point characteristic of the fluid/interior surfaces.

The light absorption point characteristic can be used to determine or confirm the type or grade of fluid flowing within the sealed pipeline by comparing the measured light absorption point with known light absorption point values of different fluids. It can also be used to determine the presence or lack thereof of particular contaminants on the interior walls of pipelines/vessels.

The fluid/interior surface is illuminated during the illuminating steps with an illumination assembly including a light source and a monochromator. Operation of the monochromator is automatically controlled to adjust the predetermined wavelength or predetermined range of wavelengths for each image, and the image recording and illuminating steps are repeated until an image having a predetermined level of clarity or contrast is identified thereby automatically tuning the monochromator to permit the probe to record additional images of the fluid illuminated at the light absorption point of the fluid. These additional images, of course, will be of great clarity and will permit further meaningful analysis of the fluid and any foreign matter carried by the fluid or the interior surfaces and any contaminants or the like on the surfaces.

The additional images taken while the fluid is illuminated with light at the light absorption point of the fluid can be analyzed to determine the characteristics of gas bubbles, solid particulates, and liquid droplets of foreign matter appearing in the images. This can be accomplished by determining a refraction index of the gas bubbles, solid particulates, and liquid droplets appearing in the images and determining the type of the foreign matter based on the refraction index measurement.

The additional images of greatest level of contrast or clarity can also be recorded at predefined elapsed intervals of time, and the movements of particles in the additional images can be analyzed to determine a velocity of flow of the fluid within the pipeline/vessel.

BRIEF DESCRIPTION OF THE DRAWINGS

The features of the present invention should become apparent from the following description when taken in conjunction with the accompanying drawings, in which.

DETAILED DESCRIPTION OF THE INVENTION

Simply for purposes of example, a fluid pumped through a sealed pipeline of a given system may be a type of crude oil or like liquid, and the present invention is directed to an apparatus and method for analyzing the fluid and its contents without disrupting the flow or an on-going process. Of course, the present invention is neither limited to evaluating crude oil nor to apparatus solely for use by the oil industry. For purposes of the present invention, the fluid can be any type of fluid that may be transferred through pipelines, conduits or the like via pumps or the like in any relevant industry. Thus, the fluid can be a liquid, slurry, powder, particulate material, resin particulate material, sand, gas or the like. Also, the present invention is not limited to pipelines and can be utilized for vessels, such as, reactors, chemical reactors, fermentors, bio-fermentors, towers, fractioning towers, tanks, vats and the like. Further, the present invention is also directed to analyzing the interior walls of the pipelines/vessels, such as during cleaning operations or the like, to identify the presence of contaminants, corrosion or the like.

Accordingly, the fluid may be some grade of crude oil or other dark, murky material that, when inspected via human eyesight with ambient light, reveals little information concerning its type, grade, and/or characteristics as well as the presence, amount, size and characteristics of foreign matter suspended within the liquid. Of course, the same is true when inspecting for contaminants or the like on interior surfaces of the pipeline/vessel. Certain types of fluids, foreign matter, contaminants, corrosion and the like may only be optically revealed under certain conditions of illumination, such as illumination with a certain wavelength or wavelength range of light, such as a certain wavelength or wavelength range of ultraviolet (UV) or infrared (IR) light/radiation.

Figure 1:
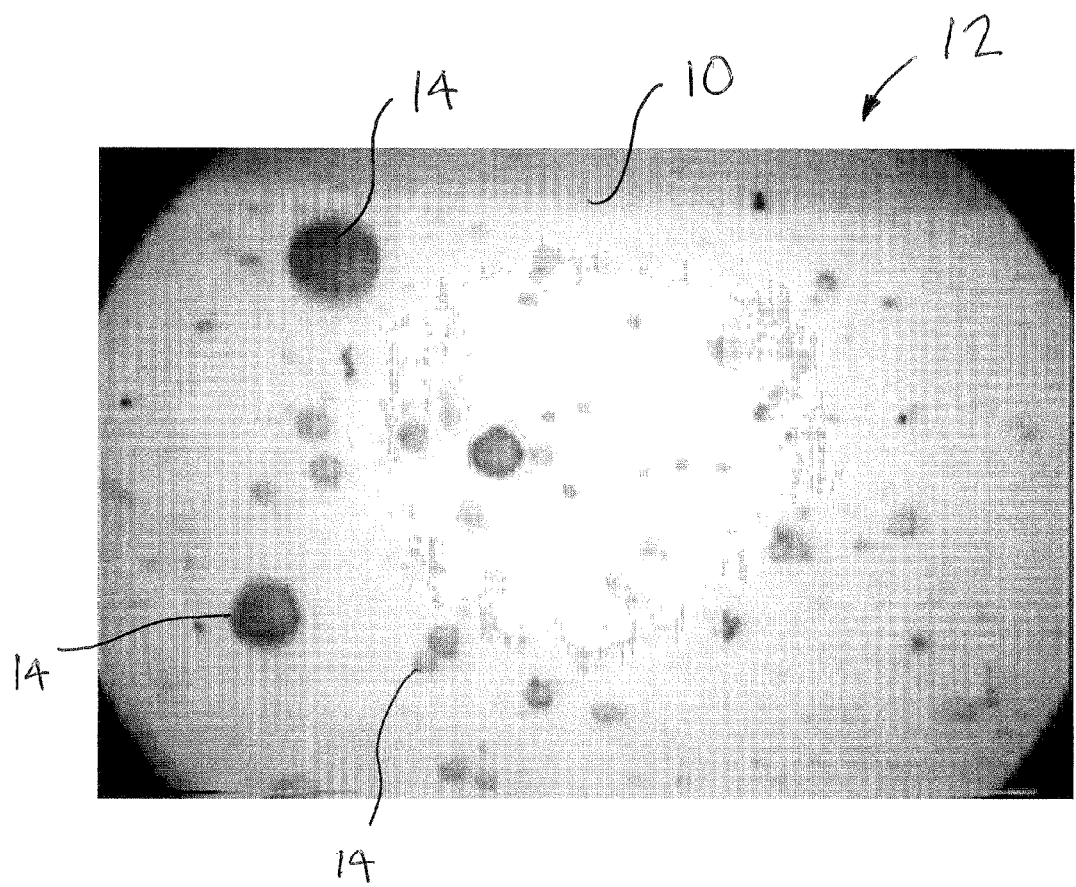
FIG. 1 is an example of an image recorded with the apparatus and method of the present invention.

FIG. 1 illustrates an example of an image 12 of a fluid 10 captured by apparatus according to the present invention as the fluid 10 is flowed within a sealed pipe or like conduit. As can be seen from FIG. 1, the present invention enables images 12 of a quality capable of ready analysis by computer imaging and recognition software or like technique for purposes of determining the type or grade of the fluid 10 and the type, size, volume and amount of foreign matter 14 within the fluid 10. Apparatus for capturing such images and methods for use in determining characteristics of the fluid 10 and foreign matter 14 from images 12 are discussed below. As an alternative, the apparatus may be used to capture images of the interior surfaces of the pipeline or vessel for inspection thereof, particularly with respect to the presence of undesirable contaminants, corrosion or the like.

Figure 2:
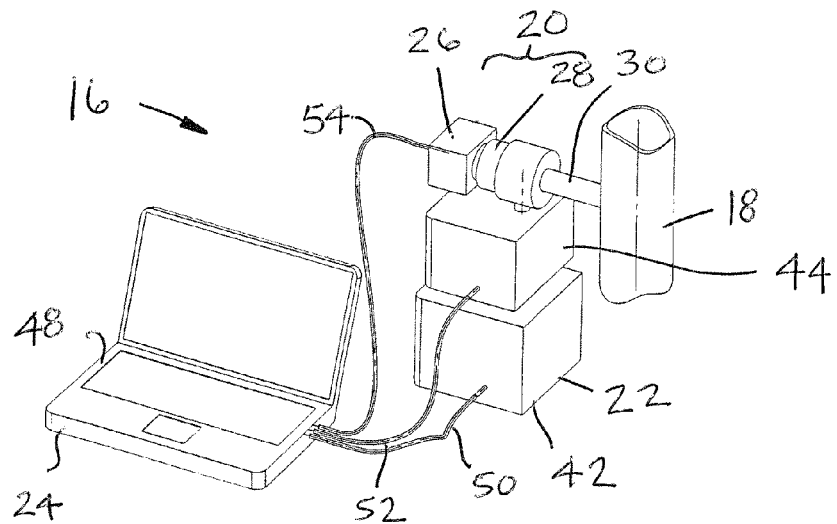
FIG. 2 is a perspective view of a "front-lit" assembly according to the present invention.
Figure 3:
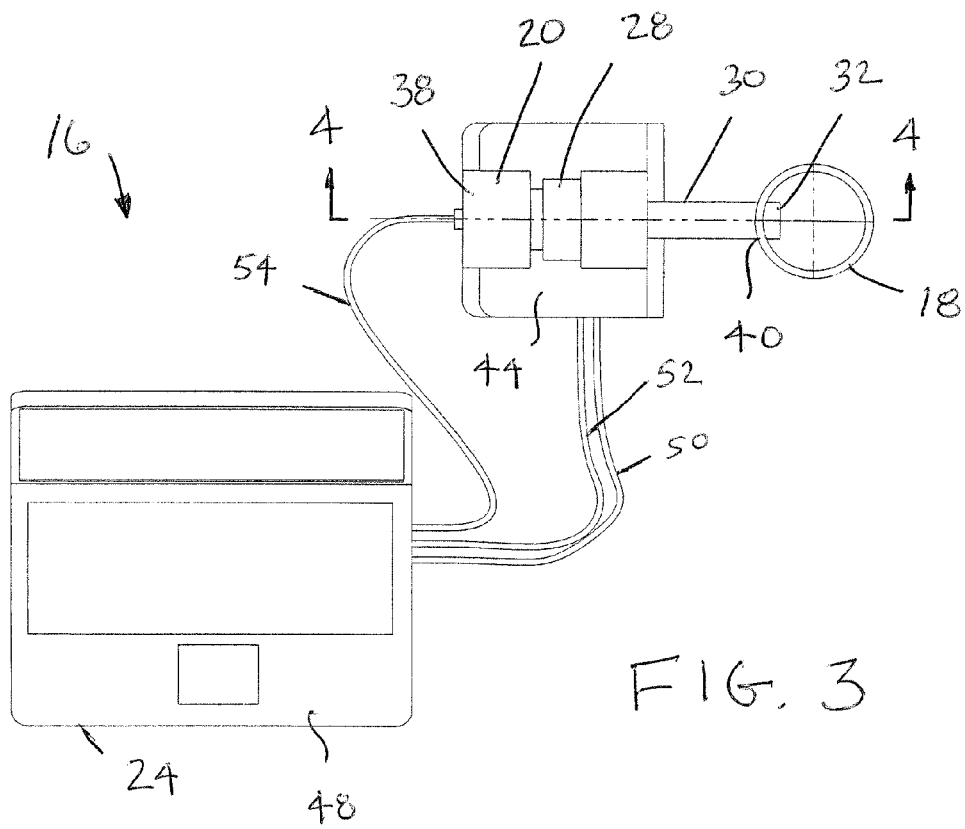
FIG. 3 is a top plan view of the assembly of FIG. 2.
Figure 4:
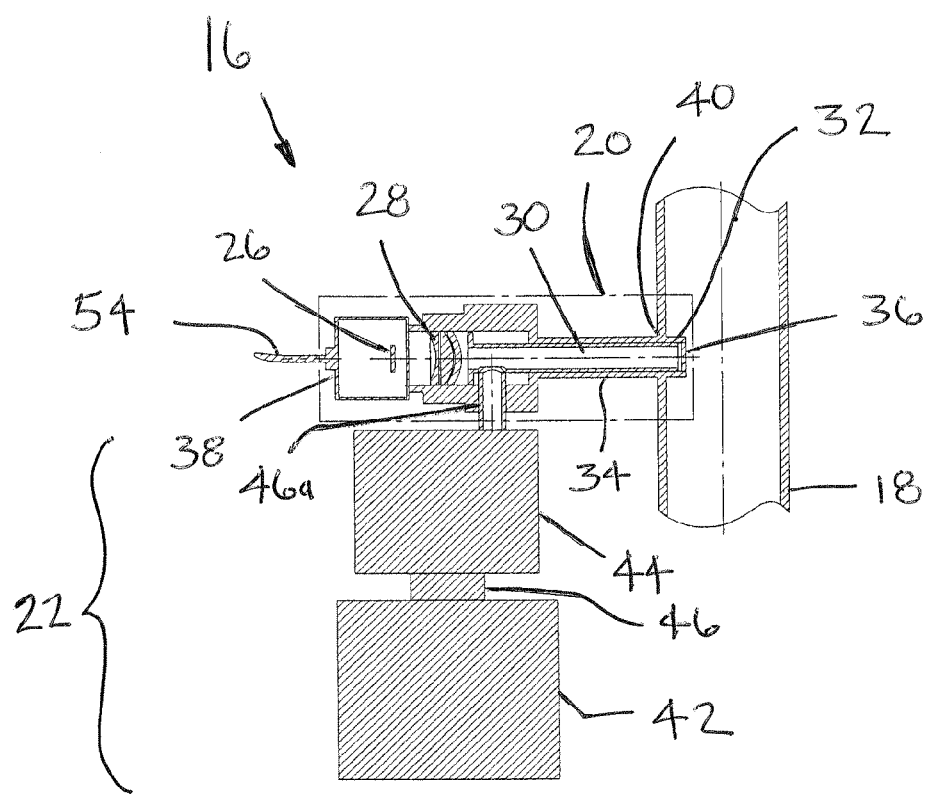
FIG. 4 is a cross-sectional view along line 4-4 of FIG. 3.

A first embodiment of an apparatus 16 according to the present invention is illustrated in FIGS. 2-4 and relates to apparatus for obtaining front-lit images of the fluid 10 and foreign matter 14 flowing within a sealed section of pipeline or the like. Of course, images of the interior walls of the pipeline/vessel can also be obtained. For purposes of ease of illustration, only a short cut-away section of a pipe 18 is illustrated in FIGS. 2-4 and the remainder of the pipeline and system to which the pipeline forms a part are not shown. A fluid, such as fluid 10, may flow through pipe 18, for instance, as part of an overall system for transporting the fluid 10 from one location to another. The pipe 18 can be of any size, diameter and length, can be made of any material, and can provide a path for flow of the fluid 10 that may be pumped by pumps (not shown) through the pipeline. Of course, the pipe can also be in the form of a vessel as discussed above.

The apparatus 16 is connected to the pipe 18 enabling images to be captured of the fluid 10 as the fluid 10 flows within the pipe 18 during normal operations without interrupting the flow or on-going operations. The apparatus 16 includes a vision probe 20, a light source assembly 22, and a controller 24. The apparatus 16 can also obtain images of the interior surfaces of the pipe 18, such as during a cleaning, maintenance, and/or inspection operation.

The vision probe 20 includes a camera or other type of sensor 26, a lens train 28, and a light/radiation transmission media or light guide 30. At least the distal end 32 of the vision probe 20 is sealed within a protective housing 34 where it extends within the pipe 18 and directly contacts the fluid 10. In most instances, when the vision probe 20 is mounted to the pipe 18, its proximal end 38 including the camera 26 and lens train 28 is located on the ambient, or external, side of the pipe 18. This enables the camera and lens assembly to be located in ambient conditions and to shield these components from potentially hostile conditions within the pipeline/vessel. If needed, the probe 20 can be gas cooled and/or heated.

Accordingly, the housing 34 is immersed within the flow of the fluid 10 within the pipe 18 and prevents the fluid 10 from entering the probe 20. Thus, the housing 34 must be able to tolerate the hostile environment within the pipeline so that it can protect the other components of the probe 20 from damage. The housing 34 can be a rigid tube of stainless steel, titanium, or other compliant material. Alternatively, the housing can have flexible bellows, joints, telescopic sections or the like so that the probe can be articulated or robotically moved to, or pointed at, an area of interest within the pipeline during an on-going operation. This may be particularly useful if capturing images at different angles relative to the direction of flow are desired and will aid in the detailed analysis of the fluid and/or foreign matter carried by the fluid.

The housing 34 of the probe 20 includes a sealed window 36, such as a high purity annealed sapphire window, through which images/readings of the fluid 10 within the pipe 18 or interior surfaces of the pipe 18 can be taken by the camera/sensor 26. As alternatives, the window 36 can be made of ruby, quartz, glass, or a synthetic material such as polycarbonate. In addition, the window 46 can include calibration markings (not shown) to aid in the determination of the size of foreign matter shown in the recorded images 12.

The camera/sensor 26 can be any device capable of taking or recording still or motion images in any format, and the lens train 28 can be provided and adjusted as desired to obtain a desired image. By way of example, the camera 26 can record black and white or color images, still images or video images and can be a charged coupled device (CCD), complementary metal oxide semiconductor (CMOS), infrared, or ultraviolet digital camera or image sensor. The digital camera/image sensor 26 is arranged at the proximal end 38 of the probe 20 to view the fluid 10 within the pipe 18 via an optical path extending through the lens train 28, transmission media 30, and window 36. The transmission media 30 can be a light guide, rod or the like or a coherent fiber optic bundle that transmits images in a coherent manner from one end to the other. The transmission media 30 can also be a gas, liquid or other solid material.

The sealed pipe 18 includes a port 40 into which the distal end 32 of the probe 20 is inserted in a manner maintaining the fluid-tight sealed integrity of the pipe 18. By way of example, the distal end 32 can be screwed into the pipe 18 with O-rings (not-shown) or the like creating a sliding seal such that the location of the window 36 within the pipe 18 can be adjusted along the length of the diameter of the pipe 18. The O-rings or gaskets can be provided in a circumferential groove of the distal end of the probe and used to form a liquid-tight seal with the port of the pipe. A fastening means (not shown) or the like can be used to lock the distal end of the probe in place in the port via a threaded connection, snap connection, flange-mount connection, compression furled connection, sanitary-flange clamp connection, or the like. Alternatively, the pipe itself can be provided with a sealed viewing window instead of an open port.

The light source assembly 22 of the apparatus 16 includes an illumination, light or radiation source 42, a monochromator 44, and optical couplings 46, such as a right angle optical coupling 46a, which interconnects to the transmission media 30 adjacent the proximal end 38 of the probe 20. This permits the transmission media 30 to transmit light or radiation originating from the light source 42 and passing through the monochromator 44 to be transmitted into the pipe 18 via window 36 and enables images that are "front-lit" to be captured by the camera/sensor 26. By way of example, the light source 42 may generate visible, infrared or ultraviolet light/radiation or may be capable of emitting different frequencies of light, such as visible light, infrared (IR), and/or ultraviolet (UV). For instance, the light source can produce near infrared (IR) light or so-called "red light" that enables better image resolution in various solutions such as opaque liquids. Light sources that emit ultraviolet (UV) light are also useful since they can provide better penetration into dark fluids and fluids of particulates. In addition, UV light is also useful for optically visualizing contaminants or the like that are only visible when they fluoresce as a result of being illuminated with specific wavelengths of UV light.

As stated above, the light/radiation generated by light source 42 must first pass through the monochromator 44 before entering the transmission media 30. A monochromator is an optical device that transmits a selectable narrow band of wavelengths of light or other radiation chosen from a wider range of wavelengths input by a light source into the device. Thus, the monochromator is a variable narrow beam frequency filter. Thus, the monochromator 44 can be set or incrementally adjusted, manually or automatically, to determine the wavelength or range of wavelengths of the light/radiation generated by the light source 20 that is permitted to enter into the transmission media 30 and pipe 18.

As best illustrated in FIG. 2, the controller 24 of the apparatus 16 can be an automated electronic control device 48, such as a computer or the like, connected via communication links 50 and 52 to the light source 42 and the monochromator 44, respectively. The control device 48 automatically controls the operation and/or timing of the light source 42 (i.e. on/off) and the wavelength or range of wavelengths of light/radiation permitted to pass into the transmission media 30 of the probe 20 and pipe 18 via the monochromator 44. The control device 48 is also connected to the camera/sensor 26 via a communication link or feed line 54 and controls the operation and timing of the camera/sensor 26 and receives images taken/recorded by the camera/sensor 26. Although the communication links 50, 52 and 54 are illustrated as wiring, these links may also be made via wireless communications to enable remote control and operation of remotely located apparatus 16 and pipelines/vessels.

The control device 48 automatically controls the capturing of numerous images/readings of the fluid 10 or surfaces illuminated at different wavelengths or ranges of wavelengths of light/radiation across a relatively wide range of wavelengths. The control device 48 can include a computer processor or like analyzing unit to analyze the recorded images in substantially real time. Information concerning the degree and/or level of contrast of the captured images can be obtained via image recognition software which may or may not be loaded in the control device 48. The information concerning the contrast level of the particular image in combination with the knowledge of the particular wavelength of light/radiation permitted to be input into the pipe 18 for the particular image can be used to readily ascertain characteristics of the fluid 10 or surfaces. For example, the image providing the greatest level of contrast, clarity or resolution provides a measurement of the light absorption point of the fluid 10. Since the light absorption point for different types/grades of fluid differs, this information can be used to confirm or determine the type/grade of fluid flowing within the pipe 18. Thus, the control device 48 utilizes and controls the operation of the camera/sensor 26 and monochromator 44 to automatically tune the apparatus 16 to produce the greatest level of clarity at the light absorption point of the fluid, thereby ascertaining the type/grade of fluid 10 and providing images of greatest clarity via which foreign matter 14 carried by the fluid 10 can be further analyzed. The automatic tuning function can be accomplished by repeatedly recording images illuminated with light/radiation of different wavelengths until a preset high level of clarity or contrast is achieved.

As illustrated in FIG. 1, after the proper wavelength of light/radiation used to illuminate the fluid 10 is determined, images 12 of great contrast, clarity and resolution can be obtained and studied. Characteristics such as the number, volume, type and shape of the foreign matter 14 can be determined from images similar to image 12 despite the fact that the liquid is dark and murky to the naked eye. Further, the refractive index of the foreign matter 14 can be ascertained at the wavelength defined by the monochromator 44. Since different substances have different refractive indexes, the type of foreign matter can be determined. For instance, a determination of the refractive index can be used to identify whether a particular piece or spot of foreign matter 14 captured in an image 12 is a water droplet, a gas bubble, a solid particulate or the like. Thus, the types of foreign matter present within the fluid can be ascertained. As discussed above, an example is to determine the presence, amount, size, etc. of particles of iron oxide within the fluid 10 which may provide an indication with respect to the operational state of an adjacent pump or like piece of equipment and when maintenance should be scheduled.

The above measurements (i.e., image capturing and analysis of the images) can be taken during normal operation of the pipeline/vessel and fluid flow through the pipe 18 or on-going process within the vessel. Thus, these measurements can be readily taken in real-time without disrupting normal operating conditions and can be readily electronically forwarded to any control location. In addition, since different types of contaminants or the like may only be optically recordable when illuminated with a known wavelength or range of wavelengths of light, their presence or lack thereof can be readily determined from images recorded while illuminated at such wavelengths of light. Thus, images of interior surfaces can be taken and analyzed for the presence of contaminants, residues, corrosion and the like.

Further, the apparatus 16 can be used to measure the velocity of flow of fluid 10 within the sealed pipe 18. For example, after image contrast has been maximized and the light absorption point of the fluid has been determined, the change of position of a particular piece of foreign material 14 carried by the fluid 10 can be ascertained via multiple images taken at preset intervals of time. The control device 48 can contain software or the like to analyze the position change relative to the elapsed period of time to determine velocity of fluid flow. Also, the focal length of the camera/sensor 26 via the lens train 28 can be varied and/or the position of the distal end 32 of the probe 20 relative to the pipe 18 can be varied to study different areas within the pipe 18 or to study particles in the flow at different angles. By way of example, flow along either of the opposite walls of pipe 18 can be studied, flow within the center of the pipe 18 can be observed, or flow at a desired angle can be observed.

Figure 5:
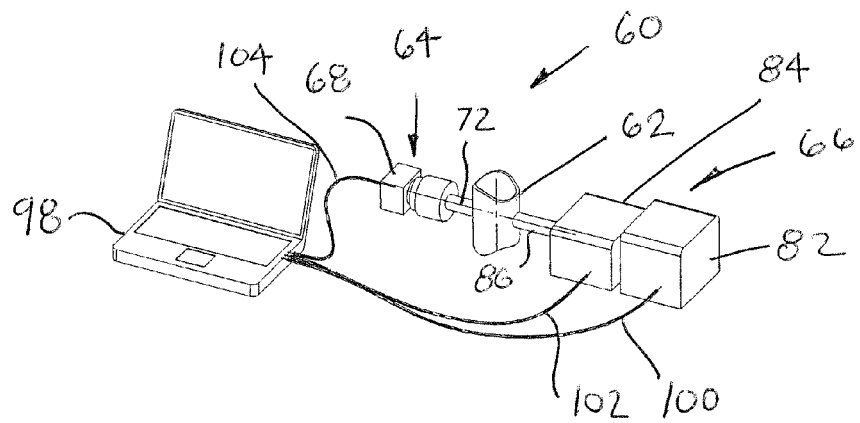
FIG. 5 is a perspective view of an alternate "back-lit" assembly according to the present invention.
Figure 7:
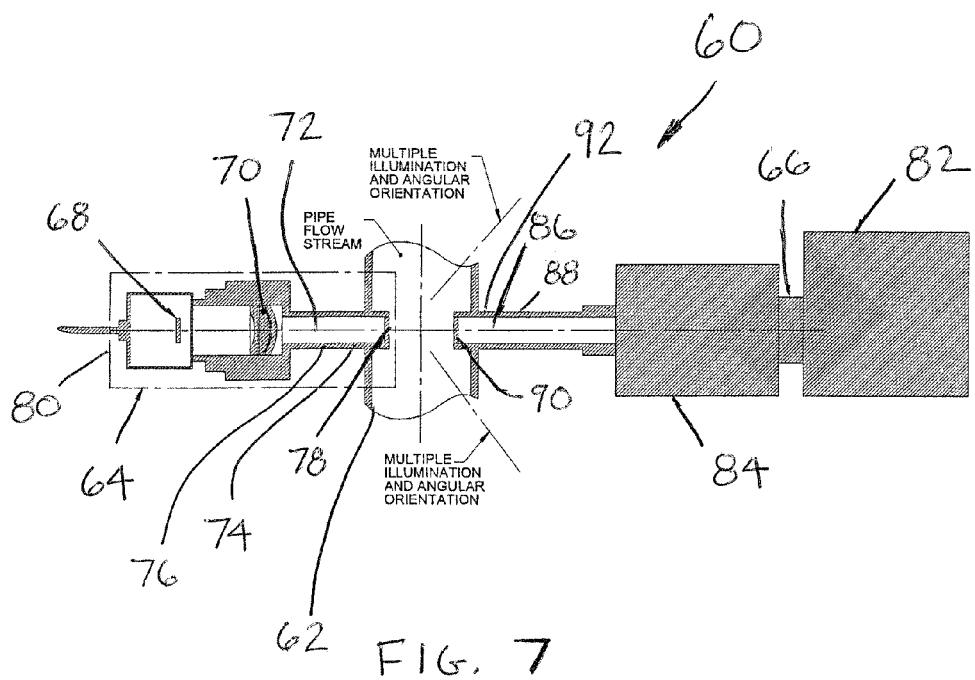
FIG. 7 is a cross-sectional view along line 7-7 of FIG. 6.
Figure 6:
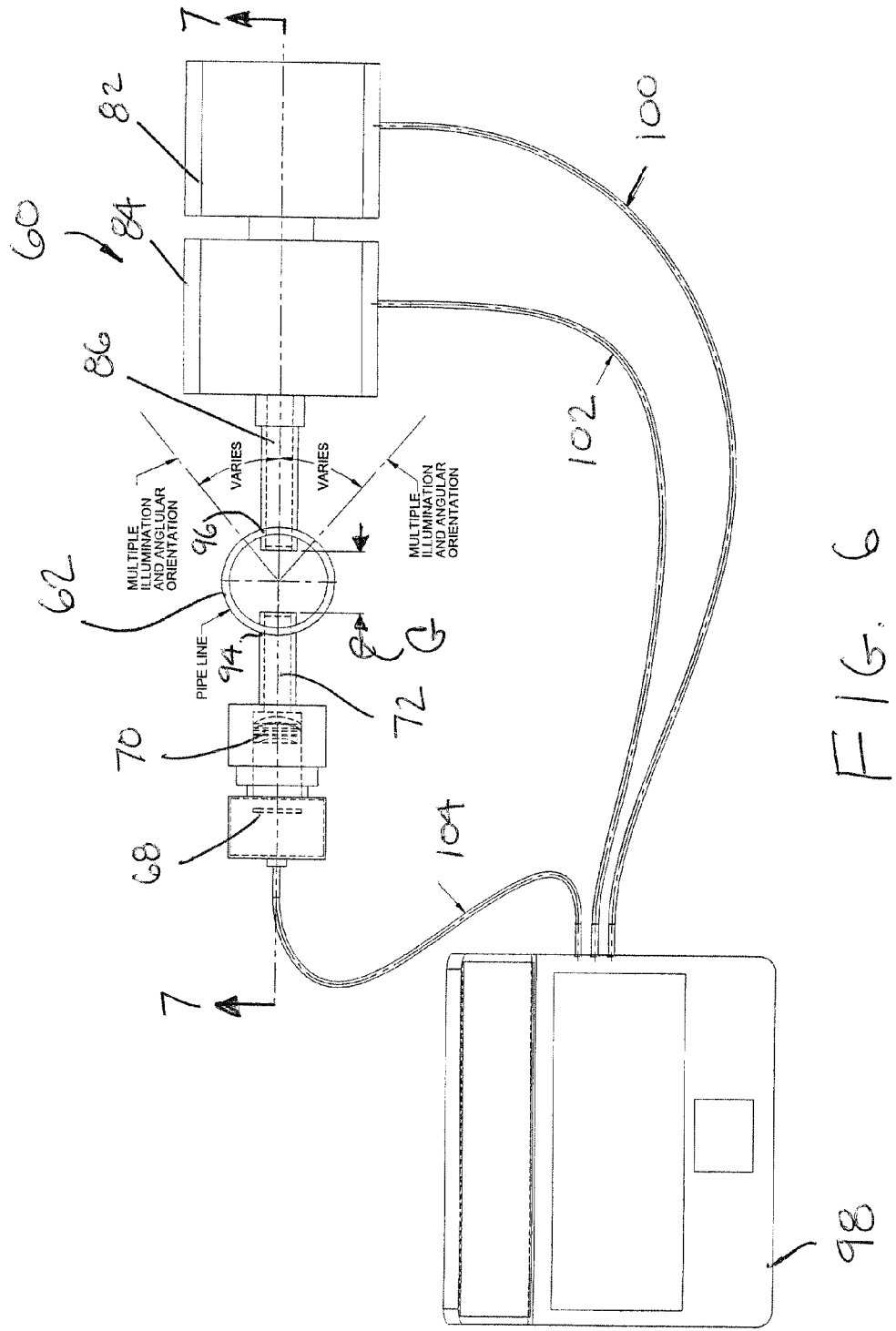
FIG. 6 is a top plan view of the assembly of FIG. 5.

A second embodiment of an apparatus 60 according to the present invention is illustrated in FIGS. 5-7 and relates to apparatus for obtaining back or side lit (i.e. at angles other than 180°) images of the fluid 10 and foreign matter 14 flowing within a pipeline/vessel or the like. For purposes of ease of illustration, only a short cut-away section of a pipe 62 is illustrated in FIGS. 5-7 and the remainder of the pipeline and system to which the pipeline forms a part are not shown. A fluid, such as fluid 10, may flow through pipe 62, for instance, as part of an overall system for transporting the fluid 10 from one location to another. The pipe 62 can be of any size, diameter, and length and can provide a path for flow of the fluid 10 that may be pumped by pumps (not shown) through the pipeline.

The apparatus 60 is connected to the pipe 62 enabling images to be captured of the fluid 10 flowing within the pipe 62. The apparatus 60 includes a vision probe 64 on one side of the pipe 62 and a light source assembly 66 on the opposite side of the pipe 62 so that "back-lit" images of the fluid 10 flowing in the sealed pipe 18 can be obtained. The probe 62 or light source assembly 66 can be adjusted so that side-lit images illuminated other than at 180° can be obtained.

The vision probe 64 includes a camera or other type of sensor 68, a lens train 70, and a light/radiation transmission media 72. At least the distal end 74 of the vision probe 64 is sealed within a protective housing 76 where it extends within the pipe 62 and directly contacts the fluid 10. The housing 76 includes a sealed window 78, such as a sapphire window, through which images/readings of the fluid 10 within the pipe 62 can be taken by the camera/sensor 68. As before, the camera/sensor 68 can be arranged at a proximal end 80 of the probe 68 to optically view the fluid 10 within the pipe 62 via an optical path extending through the lens train 70, transmission media 72, and window 78. The transmission media 72 can be a light guide such as a rod or the like.

The light source assembly 66 of the apparatus 60 includes an illumination, light or radiation source 82, a monochromator 84, and a transmission media 86 that is located within a sealed housing 88. A window 90 is located at the distal end 92 of the housing 88 to permit the light to enter the pipe 62.

The sealed pipe 62 includes a pair of opposed ports 94 and 96 into which the distal ends 74 and 92 of the probe 64 and light source assembly 66 are inserted in opposes positions in a manner maintaining the fluid-tight sealed integrity of the pipe 18 and permitting back-lit images to be taken. Of course, this arrangement can be altered if side-lit images or the like are desired. Preferably, the position of the vision probe 64 and light source assembly 66 are adjustable relative to the pipe 62 such that a desired length of gap "G" between the windows 78 and 90 can be obtained.

The light/radiation generated by light source 82 must first pass through the monochromator 84 before entering the transmission media 86. As discussed above, a monochromator is an optical device that transmits a selectable narrow band of wavelengths of light or other radiation chosen from a wider range of wavelengths input by a light source into the device. Thus, the monochromator 84 can be set manually or automatically to define the wavelength or range of wavelengths of the light/radiation generated by the light source 20 that is permitted to enter into the transmission media 86 and pipe 62.

As best illustrated in FIG. 5, a controller 98 of the apparatus 16 can be an automated electronic control device, such as a computer or the like, connected via communication links 100 and 102 to the light source 82 and the monochromator 84, respectively. The control device 98 automatically controls the operation and/or timing of the light source 82 (i.e. on/off) and the wavelength or range of wavelengths of light/radiation permitted to pass into the transmission media 86 and pipe 62 via the monochromator 84. The control device 98 is also connected to the camera/sensor 68 via a communication link or feed line 104 and controls the operation and timing of the camera/sensor 68 and receives images taken/read by the camera/sensor 68. Although the communication links 100, 102 and 104 are illustrated as wiring, these links may also be made via wireless communications to enable remote control and operation of remotely located apparatus 60.

The control device 98 automatically controls the capturing of numerous images/readings of the fluid 10 illuminated at different wavelengths or ranges of wavelengths of light/radiation across a relatively wide range of wavelengths. Information concerning the degree and/or level of contrast of the captured images can be obtained via image recognition software or other analyzing unit which may or may not be loaded in the control device 98. The information concerning the contrast level of the particular image in combination with the knowledge of the particular wavelength of light/radiation permitted to be input into the pipe 62 for the particular image can be used to readily ascertain characteristics of the fluid 10. For example, the image providing the greatest level of contrast, clarity and resolution provides an indication of the light absorption point characteristic of the fluid 10. Since the light absorption point for different types/grades of fluid differs, this information can be used to confirm or determine the type/grade of fluid flowing within the pipe 18. Thus, the control device 48 utilizes and controls the operation of the camera/sensor 68 and monochromator 84 to automatically tune the apparatus 60 to produce images of a greatest level of clarity at the light absorption point of the fluid, thereby ascertaining the type/grade of fluid 10 and providing images of greatest clarity via which foreign matter 14 carried by the fluid 10 can be further analyzed.

As illustrated in FIG. 1, after the proper wavelength of light/radiation used to illuminate the fluid 10 is determined, additional images of great contrast, clarity and resolution can be obtained and studied. Characteristics such as the number, volume, type and shape of the foreign matter 14 can be determined from images similar to image 12 despite the fact that the liquid is dark and murky to the naked eye at ambient light. Further, the refractive index of the foreign matter 14 can be ascertained at the wavelength defined by the monochromator 84. Since different substances have different refractive indexes, the type of foreign matter can be determined. For instance, a determination of the refractive index can be used to identify whether a particular piece of foreign matter 14 captured in an image 12 is a water droplet, a gas bubble, a solid particulate or the like. Thus, the types of foreign matter present within the fluid can be ascertained. As discussed above, an example is to determine the presence, amount, size, etc. of particles of iron oxide within the fluid 10 which may provide an indication with respect to the operational state of an adjacent pump or like piece of equipment and when maintenance should be scheduled.

The above measurements (i.e., image capturing and analysis of the images) can be taken during normal operation of the pipeline/vessel and fluid flow through the pipe 62. Thus, these measurements can be readily taken in real-time without disrupting normal operating conditions and can be readily electronically forwarded to any control location. Images of interior surfaces can also be obtained and analyzed.

The apparatus 60 can also be used to measure the velocity of flow of fluid 10 within the sealed pipe 62. For example, after image contrast has been maximized and the light absorption point of the fluid has been determined, the change of position of a particular piece of foreign material 14 carried by the fluid 10 can be ascertained via multiple additional images taken at preset intervals of time. The control device 98 can contain software or the like to analyze the position change relative to the elapsed period of time to determine velocity of fluid flow. Also, the focal length of the camera/sensor 68 via the lens train 70 can be varied and/or the position of the distal ends 74 and 92 of the probe 64 and light source assembly 66 and the size of the gap "G" can be adjusted.

Accordingly, the vision system of the present invention can provide remote observation, analysis, verification and historical recording of data concerning the characteristics of the fluid flowing within a sealed pipeline/vessel or interior surfaces. Such observations can include type and/or grade of fluid and characteristics of foreign matter contained within the fluid and contaminants or the like present on the surfaces of the pipeline/vessel.

The controllers of the above described apparatus preferably include an analyzing unit such as provided by image recognition and analysis software. The software can be used to provide element and constituent analysis and measurements, such as bubble/particle size, mean diameter, surface area, volume, flow rate, population, distribution, color, the ratio of surface area relative to volume, and interfacial area (i.e., amount of surface area of the bubble/particle in direct contact with liquid).

The above referenced vision probes can also carry sensors. The sensors can include temperature sensors, pressure sensors, oxygen sensors, spectrographic chemical analysis sensors, and the like. The sensors can be non-contact, optical, point-and-shoot type sensors that take readings at a focal point of the sensors. Thus, the sensors do not necessarily need to be in direct contact with the process fluid. Information from the sensors can be fed automatically to the computer processor of the controllers for analysis, verification, and/or recording. Such information can also be used to automatically adjust parameters of an on-going operation within the sealed pipeline.

The recorded images are preferably transferred to an analyzing unit such as a computer processor or the like having image recognition and analysis software. Such software analyzes the images and determines information therefrom concerning the ongoing operation in substantially real time so that corrective adjustments or the like can be made to an ongoing operation.

By way of example, and not by way of limitation, an InGaAs image sensor can be used as the camera for recording images of light/radiation within the wavelength range 1,000 nm to 2,500 nm. A particular grade or type of crude oil may provide a fluid having a light absorption point of about 1,700 nm. Thus, the apparatus and method of the present invention incrementally adjusts the wavelength of light permitted to pass through the variable narrow band frequency filter (i.e.

monochromator) within the range 1,000 nm to 2,500 nm until an image illuminated by light of wavelength of about 1,700 nm is recorded and analyzed. This image is determined to meet the high level of contrast or clarity requirements and to define the light absorption point of the fluid. From this point forward, the monochromator is tuned to this wavelength for obtaining additional images of the fluid for further analysis of the fluid and any foreign matter contained therein.

While preferred vision analysis systems and methods have been described in detail, various modifications, alterations, and changes may be made without departing from the spirit and scope of the present invention as defined in the appended claims.

The invention claimed is:

1. Apparatus for analyzing fluid within a pipeline or vessel or an interior surface of a pipeline or vessel, comprising:
   a section of pipeline/vessel having at least one viewing port;
   a probe positioned to capture images via said viewing port of fluid or interior surface within said section;
   an illumination assembly including a light source and a monochromator arranged adjacent said section to illuminate the fluid or interior surface within said section adjacent said port with visible, infrared, or ultraviolet light of a predetermined wavelength or within a predetermined range of wavelengths;
   an electronic controller in communication with said probe and said illumination assembly for automatically controlling operation of said probe and illumination assembly to capture images of the fluid or interior surface illuminated with light of different predetermined wavelength or predetermined range of wavelengths and in communication with said monochromator to control said predetermined wavelength or predetermined range of wavelengths of light permitted to pass into said section via said monochromator and to record said value or values of said predetermined wavelength or predetermined range of wavelengths relative to each image captured by said probe; and
   an analyzing unit for analyzing said images illuminated with light of different predetermined wavelength or predetermined range of wavelengths and for identifying an image of greatest level of contrast or clarity and the wavelength or predetermined range of wavelengths of the light used to illuminate the fluid for said image of greatest level of contrast or clarity;
   said analyzing unit having image recognition software for determining the level of contrast of each of said captured images so that a light absorption point of the fluid is determinable based on the wavelength or range of wavelengths of light used to illuminate the image of greatest level of contrast or clarity so that a type or grade of fluid is determined or confirmed based on the light absorption point determined for the fluid;
   said image recognition software measuring the refractive index of each spot of foreign matter appearing in the image of greatest level of contrast or clarity by comparing the measured refractive index with known refractive indexes of various foreign matter such that said image recognition software is configured to determine the presence, type, and characteristics of gas bubbles, solid particulates, and liquid droplets of foreign matter in the fluid; and
   said controller and said analyzing unit being provided as modules of a computer linked to said camera of said probe, said monochromator, and said light source for controlling the operation thereof and for receiving and recording images taken by said camera in real time for being analyzed in real time by said image recognition software;
   wherein said analyzing unit being configured to detect an amount of solid particulates of iron oxide in the fluid and to automatically schedule or delay maintenance of an adjacent piece of equipment or pump based on the detected amount of iron oxide.

2. Apparatus according to claim 1, wherein said probe includes a camera, a lens train, and a light guide, wherein a distal end of said light guide is encapsulated within a sealed housing having a window, and wherein said housing is inserted into said port and forms a fluid-tight seal therewith.

3. Apparatus according to claim 2, further comprising an optical coupling for coupling said illumination assembly to said light guide of said probe.

4. Apparatus according to claim 2, wherein said pipeline has a separate illumination port to which said illumination assembly is coupled.

5. Apparatus according to claim 1, wherein said probe includes a non-contact optical sensor selected from the group consisting of a temperature sensor, a pressure sensor, and chemical analysis sensor.

6. A method of analyzing fluid within a pipeline or vessel, comprising the steps of:
   recording an image of fluid within the pipeline or vessel with an optical probe via a viewing port of said pipeline or vessel;
   during said recording step, illuminating the fluid adjacent the viewing port with light of a predetermined wavelength or predetermined range of wavelengths and recording the value or values of the predetermined wavelength or predetermined range of wavelengths for the image, said illuminating step being accomplished with an illumination assembly including a light source and a monochromator, operation of the monochromator being automatically controlled to adjust the predetermined wavelength or predetermined range of wavelengths for each image;
   repeating said illuminating and image recording steps a plurality of times in which each illuminating step is accomplished with light of different predetermined wavelength or predetermined range of wavelengths;
   determining which recorded image is of greatest contrast or clarity to thereby identify a light absorption point of the fluid;
   after said light absorption of the fluid is identified, determining a type or grade of the fluid within the pipeline or vessel based on the identified light absorption point by comparing the identified light absorption point with a set of known light absorption point values of different fluids and automatically tuning the monochromator to cause the probe to record additional images of the fluid illuminated at the identified light absorption point of the fluid; and
   detecting a refraction index of foreign matter appearing in said additional images to identify a type of the foreign matter in the fluid;
   wherein the foreign matter being detected during said detecting step is iron oxide particulate matter, and further comprising the step of determining an operational state of an adjacent piece of equipment or pump based on an amount of iron oxide particulate matter detected; and
   the step of reducing or extending a scheduled time period between performing maintenance to the adjacent piece of equipment or pump based on the amount of iron oxide particulate matter detected during said detecting step.

7. A method according to claim 6, wherein said additional images are recorded at predefined elapsed intervals of time at the light absorption point of the fluid after said step of identifying said light absorption point, and further comprising the step of analyzing movements of particles in said additional images to determine velocity of flow of the fluid within the pipeline or vessel.

8. A method according to claim 6, wherein the fluid is crude oil.

9. A method according to claim 6, wherein said light is visible, infrared, or ultraviolet light.

* * * * *